(12) United States Patent
Chen et al.

(10) Patent No.: US 12,635,983 B2
(45) Date of Patent: May 26, 2026

(54) APPARATUS FOR DISPLAYING A PLURALITY OF SLICES OF THREE-DIMENSIONAL ULTRASOUND SCAN DATA

(71) Applicant: KONINKLIJKE PHILIPS N.V., Eindhoven (NL)

(72) Inventors: Jin Ning Chen, Fuzhou (CN); Jingping Xu, Shanghai (CN); Wen Zhong, Shenyang (CN); Xianghui Bai, Shanghai (CN); Yishuang Meng, Shanghai (CN); Vivian Wei, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 155 days.

(21) Appl. No.: 18/216,235

(22) Filed: Jun. 29, 2023

(65) Prior Publication Data

US 2024/0000430 A1 Jan. 4, 2024

(30) Foreign Application Priority Data

Jun. 30, 2022 (WO) ................ PCT/CN2022/102670

(51) Int. Cl.
*A61B 8/00* (2006.01)
*A61B 8/08* (2006.01)
(52) U.S. Cl.
CPC .............. *A61B 8/463* (2013.01); *A61B 8/085* (2013.01); *A61B 8/466* (2013.01); *A61B 8/469* (2013.01); *A61B 8/483* (2013.01)

(58) Field of Classification Search
CPC ......... A61B 8/483; A61B 8/466; A61B 8/463; A61B 8/469; A61B 8/523; A61B 8/467;
(Continued)

(56) References Cited

U.S. PATENT DOCUMENTS 5,997,479 A 12/1999 Savord et al.
6,013,032 A 1/2000 Savord
(Continued)

OTHER PUBLICATIONS

Turel Fatakia, F., et al. "How repeatable is assessment of external anal sphincter trauma by exoanal 4D ultrasound?. " Ultrasound in Obstetrics & Gynecology 53.6 (2019): 836-840. (Year: 2019).*
(Continued)

*Primary Examiner* — Joseph M Santos Rodriguez
*Assistant Examiner* — Jason P Gross

(57) ABSTRACT

An apparatus for processing ultrasound scan data comprises a processor configured to obtain three-dimensional ultrasound scan data for a volume including a region of interest in a subject, the processor is further configured to: provide the three-dimensional ultrasound scan data for display to the user by providing for display to the user a first two-dimensional view of the region of interest in a predetermined direction such that the first two-dimensional view intersects the first boundary; and upon receiving, via the user interface, a user input indicating a location of the first boundary in the first two-dimensional view of the region of interest, generate a second two-dimensional view of the region of interest corresponding to the slice at the first boundary on basis of the indicated location, and providing for display to the user the second two-dimensional view of the region of interest.

13 Claims, 6 Drawing Sheets

(58) Field of Classification Search
CPC .. A61B 8/13; A61B 8/465; A61B 8/46; G06T
2207/10136; G01S 15/8993
See application file for complete search history.

(56)                    References Cited

U.S. PATENT DOCUMENTS

| | | | |
|---|---|---|---|
| 6,283,919 | B1 | 9/2001 | Roundhill et al. |
| 6,458,083 | B1 | 10/2002 | Jago et al. |
| 6,623,432 | B2 | 9/2003 | Powers et al. |
| 7,853,304 | B2 * | 12/2010 | Bauman .................. G06T 15/08 600/407 |
| 7,946,989 | B2 * | 5/2011 | Hasegawa .............. A61B 8/463 600/443 |
| 2005/0049494 | A1 * | 3/2005 | Gritzky .................. A61B 8/483 600/453 |
| 2006/0034513 | A1 * | 2/2006 | Cai ......................... A61B 8/523 382/173 |
| 2009/0267940 | A1 * | 10/2009 | Garg ....................... G06T 15/08 345/419 |
| 2010/0280375 | A1 * | 11/2010 | Zhang .................. A61B 8/4281 600/443 |
| 2011/0141110 | A1 * | 6/2011 | Vion ................... G01S 15/8993 382/131 |
| 2011/0282207 | A1 * | 11/2011 | Hashimoto ............ A61B 8/466 600/443 |
| 2013/0012820 | A1 * | 1/2013 | Brown ................... A61B 8/483 600/443 |
| 2014/0050381 | A1 * | 2/2014 | Lee ...................... A61B 8/5292 600/437 |
| 2014/0059486 | A1 * | 2/2014 | Sasaki .................. A61B 8/0866 715/810 |
| 2015/0227274 | A1 * | 8/2015 | Lee ........................ G06F 1/3265 715/776 |
| 2015/0262353 | A1 * | 9/2015 | Yoo ......................... A61B 8/483 382/128 |
| 2015/0305718 | A1 * | 10/2015 | Ogasawara ............ A61B 8/466 600/440 |
| 2015/0365306 | A1 * | 12/2015 | Chaudhri ......... H04N 21/47205 715/753 |
| 2016/0030003 | A1 * | 2/2016 | Liu ......................... A61B 8/145 600/443 |
| 2016/0042248 | A1 * | 2/2016 | Endo ...................... A61B 8/523 382/131 |
| 2016/0151048 | A1 * | 6/2016 | Lee ........................ A61B 8/466 600/437 |
| 2016/0239203 | A1 * | 8/2016 | Sato .................... G06F 3/04883 |
| 2017/0172538 | A1 * | 6/2017 | Kristoffersen ........... A61B 8/06 |
| 2017/0325783 | A1 * | 11/2017 | White .................. A61B 5/1073 |
| 2018/0321843 | A1 * | 11/2018 | Giannotti ........... G06F 3/04886 |
| 2020/0113541 | A1 * | 4/2020 | Kato .................... A61B 5/0095 |

OTHER PUBLICATIONS

Bahrami, S. et al., "Pelvic floor ultrasound: when, why, and how?", Abdom Radiol, 2021, vol. 46, Issue 4, pp. 1395-1413.
Anonymous, "AIUM/IUGA Practice Parameter for the Performance of Urogynecological Ultrasound Examinations: Developed in Collaboration with the ACR, the AUGS, the AUA, and the SRU", J Ultrasound Med., 2019, Issue 4, pp. 851-864.
Dietz, H.P., "Exoanal Imaging of the Anal Sphincters", J Ultrasound Med, 2018, vol. 37, Issue 1, pp. 263-280.

* cited by examiner

APPARATUS FOR DISPLAYING A PLURALITY OF SLICES OF THREE-DIMENSIONAL ULTRASOUND SCAN DATA

CROSS-REFERENCE TO PRIOR APPLICATIONS

This application claims the benefit of European Application No. 22194328.5, filed Sep. 7, 2022, and Chinese Application No. PCT/CN2022/102670, filed Jun. 30, 2022, all of which are hereby incorporated by reference herein.

FIELD OF THE INVENTION

The invention relates to processing ultrasound scan data and, more particularly, to automatically selecting a portion of ultrasound scan data to be processed.

BACKGROUND OF THE INVENTION

Pelvic floor disorders are a significant medical issue, encompassing a number of prevalent conditions and including pelvic organ prolapse, urinary and fecal incontinence, obstructed defecation, and sexual dysfunction. Ultrasound is one of the major imaging modalities that can be used to assess pelvic floor function.

One step of a pelvic floor ultrasound examination is to perform an evaluation of the anal sphincter, specifically the internal anal sphincter (IAS) integrity, and the external anal sphincter (EAS) integrity. The anal canal includes the anal mucosa, the IAS, the EAS, and the puborectalis muscle.

An ultrasound scan may generate scan data representing a three-dimensional region (i.e., a volume) of the subject being scanned, for example the anal sphincter. In existing systems, assessment of the scan data may involve a repetitive and time-consuming manual process of identifying relevant slices of the scan data. Such a process can occupy significant time of a medical professional, requiring manipulation of the data, and multiple iterations until the desired slices of data are identified.

US 20170172538A1 disclosed a user interface defines a proximal plane and a distal plane within the ultrasound data that are parallel to one another. US 20130012820A1 disclosed an ultrasound probe acquires a 3D image dataset of a volumetric region of the body and the 3D image data is reformatted into a sequence of successive parallel image planes extending in one of three orthogonal directions through the volume. US 20150262353A1 disclosed a method of changing at least one of a direction and position of a plane selection line for acquiring an image of a plane of interest of an object.

There is therefore a desire for an improved system which enables a medical professional to identify more quickly and/or accurately the relevant slices of three-dimensional scan data to be used for a medical assessment.

SUMMARY OF THE INVENTION

The inventors of the present disclosure have recognized that the processing of three-dimensional ultrasound data can be improved by automating the selection of the slices to be presented to the medical professional, so that the medical professional is not required to perform an iterative process of locating the region of interest within the scan data. According to the present disclosure, a medical professional (e.g., a clinician) is able to select at least one of a first end boundary of the relevant portion of data (e.g., the region of interest) and a second end boundary of the relevant portion of data from an assessment of the scan data from two different views. In some embodiments, both first and second end boundary are identified based on user inputs (e.g. selected by a medical professional via one or more user inputs), whilst in some other embodiments, one of the end boundaries is identified based on user inputs, and the other is automatically identified without additional user inputs. Once the end boundaries have been identified, the system disclosed herein automatically divides the volume defined by the end boundaries in a defined number of slices, and generates an image corresponding to each slice. In other words, the disclosed system automatically generates a set of spaced images (e.g. equally-spaced) showing through the volume between the end boundaries. When displayed to a user (e.g., a medical professional), the images can be used to medically assess the region of interest captured in the ultrasound data.

The invention is defined by the independent claims. The dependent claims define advantageous embodiments.

According to a first specific aspect, there is provided an apparatus for processing ultrasound scan data comprising a processor configured to obtain three-dimensional ultrasound scan data for a volume including a region of interest in a subject; provide the three-dimensional ultrasound scan data for display to a user; receive, via a user interface, an indication of a first boundary of the three-dimensional ultrasound scan data; receive an indication of a second boundary of the three-dimensional ultrasound scan data; generate, from the three-dimensional ultrasound scan data, a plurality of images, each of the plurality of images corresponding to a respective one of a plurality of slices spaced between the first and second boundaries, the plurality of slices comprising a slice at the first boundary; and provide the plurality of images for display to the user. In particular, providing the three-dimensional ultrasound scan data for display to the user may comprise providing for display to the user a first two-dimensional view of the region of interest in a first direction. The first direction is predetermined such that the first two-dimensional view at least intersects the first boundary. In some embodiments, the first two-dimensional view is perpendicular to the slice at the first boundary. In some embodiments, the first two-dimensional view intersects each of the plurality of slices. That is, the plurality of slices are inclined to the first two-dimensional view. In some embodiments, each of the plurality of slices is perpendicular to the first two-dimensional view. The processor is further configured to, upon receiving, via the user interface, a user input indicating a location of the first boundary in the first two-dimensional view of the region of interest, generate a second two-dimensional view of the region of interest corresponding to the slice at the first boundary on basis of the indicated location, and providing for display to the user the second two-dimensional view of the region of interest.

In some embodiments, the processor is further configured to generate the plurality of images upon a triggering signal. The trigger signal can be generated upon receiving a further user input for triggering the generation of the plurality of images, and/or can be automatically generated in accordance with a pre-determined rule. For example, the triggering can be generated if no further user input for indicating the location(s) of the first and/or the second boundaries is received with a pre-determined time period.

In some embodiments, the processor may be configured to provide for display to the user, along with the plurality of generated images, the first two-dimensional view of the region of interest including an indication of the location in the first two-dimensional view corresponding to each of the generated images.

The region of interest may comprise the anal sphincter of the subject.

In some embodiments, the indication of the first boundary of the three-dimensional ultrasound scan data comprises an indication of a view of the anal sphincter that corresponds to the most cranial slice of the anal sphincter that does not include the external anal sphincter ventrally. The indication of the second boundary of the three-dimensional ultrasound scan data may comprise an indication of a view of the anal sphincter that corresponds to the most dorsal slice of the anal sphincter that does not include the internal anal sphincter.

The processor may, in some embodiments, be configured to receive, via the user interface, an indication of a number of images to be generated as the plurality of images. The number of images generated as the plurality of images may be equal to the indicated number of images.

The apparatus may further comprise a user interface via which one or more user inputs may be made.

According to a second specific aspect, there is provided an ultrasound scanning system comprising an apparatus as disclosed herein.

According to a third specific aspect, there is provided a computer-implemented method for processing ultrasound scan data comprising obtaining three-dimensional ultrasound scan data for a volume including a region of interest in a subject; providing the three-dimensional ultrasound scan data for display to a user; receiving, via a user interface, an indication of a first boundary of the three-dimensional ultrasound scan data; receiving an indication of a second boundary of the three-dimensional ultrasound scan data; generating, from the three-dimensional ultrasound scan data, a plurality of images, each of the plurality of images corresponding to a respective one of a plurality of slices spaced between the first and second boundaries, the plurality of slices comprising a slice at the first boundary; and providing the plurality of images for display to the user. In particular, the step of providing the three-dimensional ultrasound scan data for display to a user may comprise providing for display to the user a first two-dimensional view of the region of interest in a predetermined direction such that the first two-dimensional view at least intersects the first boundary. The method may further comprise receiving, via a user interface, a user input indicating a location of the first boundary in the first two-dimensional view of the region of interest, generating a second two-dimensional view of the region of interest corresponding to the slice at the first boundary on basis of the indicated location, and providing for display to the user a second two-dimensional view of the region of interest corresponding to the indicated location.

The method may, in some embodiments, further comprise providing for display to the user, along with the plurality of generated images, the first two-dimensional view of the region of interest including an indication of the location in the first two-dimensional view corresponding to each of the generated images.

The method may further comprise receiving, via the user interface, an indication of a number of images to be generated as the plurality of images. In some embodiments, the number of images generated as the plurality of images may be equal to the indicated number of images.

In some embodiments, the region of interest comprises the anal sphincter of the subject. The number of images generated in the plurality of images may be 8. The generated images may be provided for display to the user in a grid arrangement.

According to a fourth specific aspect, there is provided a computer program product comprising computer-readable code that is configured such that, on execution by a suitable computer or processor, the computer or processor is caused to perform any of the methods disclosed herein.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1:
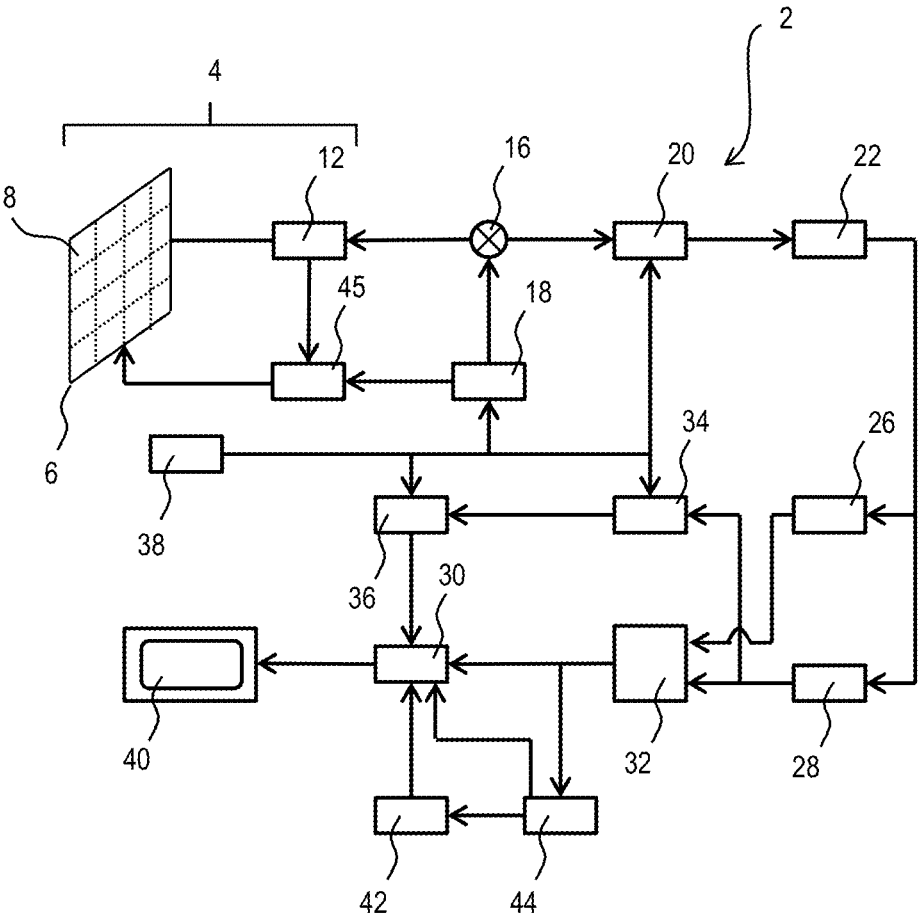
FIG. 1 is a schematic illustration of an example of an ultrasound system.

According to various embodiments, the present disclosure provides a mechanism by which relevant images can be extracted from a three-dimensional dataset, based on a user selection of some boundary limits. Images corresponding to a set of spaced slices between the chosen end boundaries are extracted automatically and presented to the user, which avoids the need for the user to iteratively review the three-dimensional data and identify the appropriate images to extract.

Embodiments of the invention relates to ultrasound scan data (i.e., scan data obtained via an ultrasound scan). Before discussing the invention in detail, the general operation of an exemplary ultrasound system 2 will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three-dimensional volume of a region of interest. In another example, the transducer array may be a 1D array.

The transducer array 6 is coupled to a micro-beamformer 12 which controls reception of signals by the transducer elements. Micro-beamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the micro-beamformer is entirely optional. Further, the system includes a transmit/receive (T/R) switch 16, which the micro-beamformer 12 can be coupled to and which switches the array between transmission and reception modes, and protects the main beam-former 20 from high energy transmit signals in the case where a micro-beamformer is not used and the transducer array is operated directly by the main system beamformer. The transmission of ultrasound beams from the transducer array 6 is directed by a transducer controller 18 coupled to the micro-beamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a micro-beamformer) during the transmission mode.

In a typical line-by-line imaging sequence, the beamforming system within the probe may operate as follows. During transmission, the beamformer (which may be the micro-beamformer or the main system beamformer depending upon the implementation) activates the transducer array, or a sub-aperture of the transducer array. The sub-aperture may be a one-dimensional line of transducers or a two-dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated, and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above-described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the micro-beamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of non-linear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g., the harmonics of the main harmonic).

The RF signals may then be coupled to a B mode (i.e., brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two-dimensional (2D) sector-shaped format, or a pyramidal three-dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes, the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
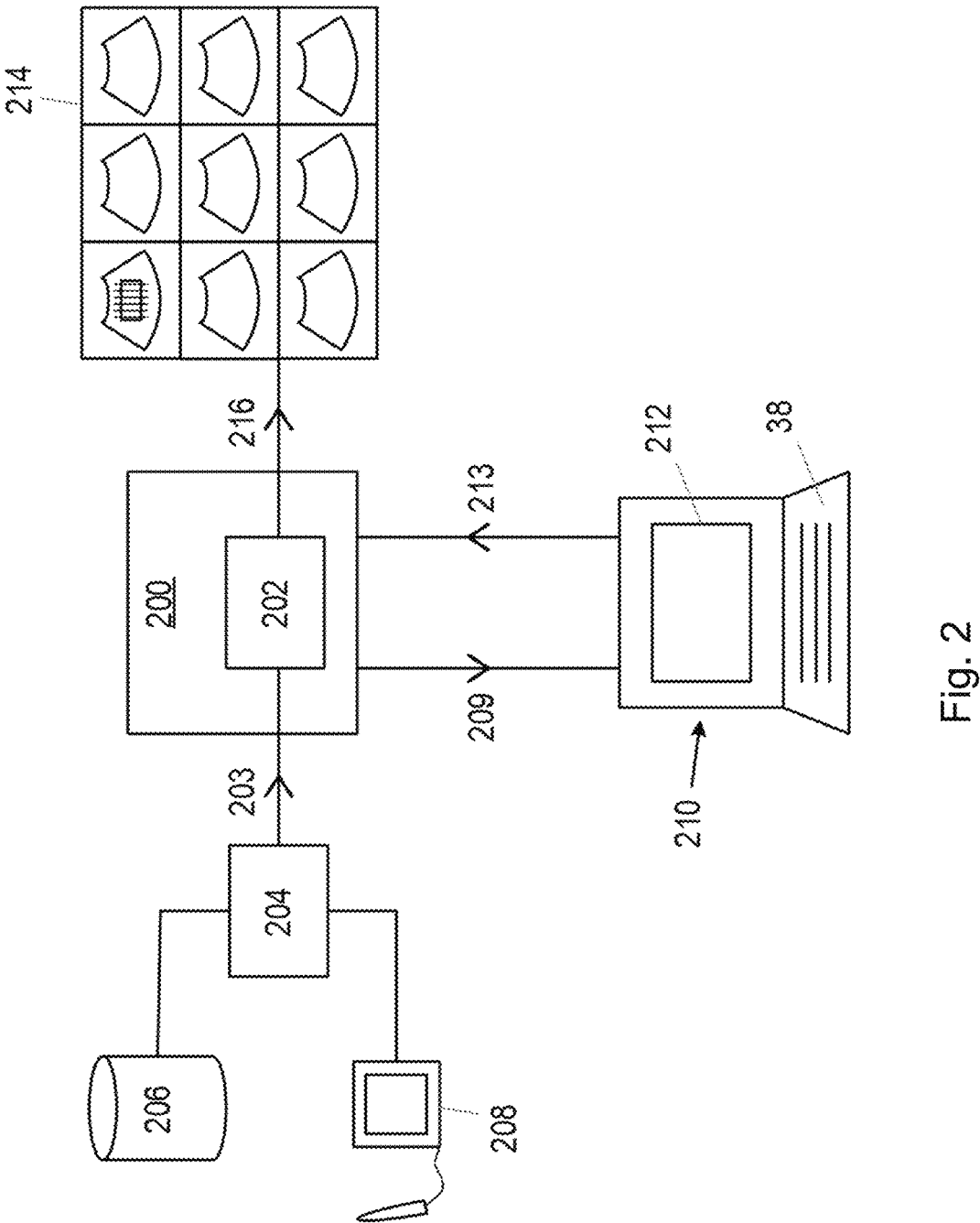
FIG. 2 is a schematic illustration of an example of an apparatus for processing ultrasound scan data.

According to a first aspect, the present invention relates to an apparatus. FIG. 2 is a schematic illustration of an example of an apparatus 200 for processing ultrasound scan data. The apparatus 200 comprises a processor 202, which may comprise, include and/or the in operative communication with one or more of the B-mode processor 26, the Doppler processor 28, the image processor 30, the quantification processor 34, the graphics processor 36, or any other controller or processing apparatus disclosed herein. The processor 202 may perform functions of one or more of the other processors disclosed herein. The processor 202 is configured to obtain 203 three-dimensional ultrasound scan data 204 for a volume including a region of interest in a subject. The three-dimensional ultrasound scan data 204 may, in some embodiments, be received from a database 206 containing previously acquired scan data, or directly from an ultrasound scan device 208, for example if the scan data is to be acquired and processed in real-time. The term "three-dimensional ultrasound scan data" is intended to refer to scan data acquired in respect of a volume of a person's body (e.g., tissue and/or bone), and may include a series of discrete "slices" of data which, together, constitute the volume. The term "region of interest" as used herein is intended to refer to a region (e.g., part, portion or sub-volume) of the volume of the person's body that is to be viewed, inspected or analyzed in greater detail. In one particular embodiment, the region of interest may comprise the anal sphincter of the subject. However, it will be appreciated that, in other embodiments, the region of interest may include any other part of the subject that is to be viewed and/or assessed.

The three-dimensional ultrasound scan data 204 may be acquired using known scanning techniques, as discussed above, and the data may be represented as one or more two-dimensional images. In some examples, the three-dimensional ultrasound scan data 204 may be described or represented as three planes—an A-plane which is parallel to the acquisition plane, a B-plane which is perpendicular to the A-plane and parallel to the ultrasound beam, and a C-plane (sometimes referred to as a coronal plane), perpendicular to the A-plane and the B-plane. These planes may be referred to as multiplanar reconstruction (MPR) planes.

The processor 202 is configured to provide 209 the three-dimensional ultrasound scan data 204 for display to a user. The three-dimensional ultrasound scan data 204 may, for example, be displayed using the computing device 210 that includes at least a display 212 and a user interface, such as the user interface 38. The three-dimensional ultrasound scan data 204 may be viewed in various ways, and through various planes, such as the A-, B- and C-planes discussed above. According to the present disclosure, the three-dimensional data 204 may be displayed to a user (e.g., a medical professional) in a first plane to enable them to identify end boundaries, and the plurality of images may be selected, based on the defined end boundaries, in a second plane. For example, in one example, providing the three-dimensional ultrasound scan data for display to the user may comprise providing for display to the user a first two-dimensional view of the region of interest in a predetermined first direction. The first two-dimensional view in the first direction may, for example, comprise a view through the A-plane, the B-plane or the C-plane as discussed above, or a sagittal view, a transverse view or a coronal view of the region of interest. A sagittal view is a view through a sagittal plane, which divides the body into left and right parts; a transverse view is a view through a transverse plane, which divides the body into superior (e.g., upper) and inferior (e.g., lower) parts; and a coronal view is a view through the coronal plane, which divides the body into upper and lower parts. In some examples, the first two-dimensional view may comprise a midsagittal view, which is a view through the midsagittal plane, which divides the body centrally into two relatively equal halves—a left half and a right half. In an example in which the region of interest comprises an anal sphincter, a sagittal view may enable a user to see the length of the anal sphincter.

According to the present invention, providing the three-dimensional ultrasound scan data for display to the user may comprise, upon receiving a user input indicating the location of the first boundary in the first two-dimensional view, generating a second two-dimensional view of the region of interest corresponding to the slice at the first boundary on basis of the indicated location, and providing for display to the user a second two-dimensional view of the region of interest. In this way, the slice at the first boundary (called boundary slice) is displayed to the user upon the user indication of the first boundary, which allows the user to provide further user input for adjusting the location of the first boundary based on the displayed boundary slice.

In some embodiments, the second two-dimensional view may be in a direction that is perpendicular to the first two-dimensional view, and may, for example, comprise a view through the A-plane, the B-plane or the C-plane as discussed above, or a sagittal view, a transverse view or a coronal view of the region of interest. For example, the first two-dimensional view may comprise a view through the B-plane or a sagittal view and the second two-dimensional view may comprise a view through the C-plane a transverse view. In some examples, the second two-dimensional view may be along a predetermined direction (e.g., in a vertical direction) in the first two-dimensional view. In other examples, the first two-dimensional view and/or the second two-dimensional view may comprise any cross-sectional view of the region of interest. In some examples, a third two-dimensional view, in a direction which is perpendicular to the first and second directions, may be provided for display to the user. In an example in which the region of interest comprises an anal sphincter, a transverse view provides a cross-sectional view through the anal sphincter, enabling the user to identify the ends (e.g., the beginning and the end) of muscles associated with or forming part of the anal sphincter, such as the internal anal sphincter (IAS) and the external anal sphincter (EAS).

In some embodiments, providing the three-dimensional ultrasound scan data for display to the user may comprise providing for display a first two-dimensional view (e.g., a sagittal view) and one or more second two-dimensional views (e.g., transverse views) of the region of interest. For example, the sagittal view may show the entire length of the region of interest (e.g., an anal sphincter) and the one or more transverse views may show sectional views at various points through of the region of interest. The first (e.g., sagittal) view and the one or more second (e.g., transverse) views may be displayed together on a display screen, for example side-by-side.

In some embodiments, the apparatus 200 may further comprise a user interface (e.g., the user interface 38) via which one or more inputs may be made. In other embodiments, as noted above, such a user interface may be remote from the apparatus (e.g., forming part of the computing device 210) and may communicate with the processor 202 to provide user inputs it receives.

The processor 202 is configured to receive 213, via a user interface (e.g., the user interface 38), an indication of a first boundary of the three-dimensional ultrasound scan data. The processor 202 is also configured to receive 213, via the user interface (e.g., the user interface 38), an indication of a second boundary of the three-dimensional ultrasound scan data. The first and second boundaries may, for example, comprise boundaries of the region of interest, such as end boundaries of the region of interest. In an example in which the region of interest comprises the anal sphincter, the first boundary may comprise a first end of the region of interest, such as the anal sphincter (e.g., a first end of the IAS or the EAS) and the second boundary may comprise a second end of the region of interest, such as the anal sphincter (e.g., a second end of the IAS or the EAS).

The indication of the first boundary and the second boundary may be provided by various mechanisms, for example by a user (e.g., medical professional) selecting a position on an image of the three-dimensional ultrasound scan data by moving a cursor and selecting points in the image corresponding to the first and second boundaries. In other examples, selection of the first boundary and the second boundary may be made using an input via a keyboard, a touchpad, a touchscreen, a microphone, or the like.

Once the boundaries have been received by the processor 202, the processor is able to generate a set of images, between the first boundary and the second boundary. These images may be equidistant from each other, i.e. equal spacing, or spaced in any other form, e.g. cosine spacing or logarithmic spacing. The three-dimensional ultrasound scan data may be considered to be a set of slices of scan data which, together, form the volume captured in the three-dimensional ultrasound scan data. Each image in the set of images generated by the processor 202 may correspond to one of the slices. Within the set of images that are generated, one image may correspond to the slice of data at the first boundary and another image may correspond to the slice of data at the second boundary. The remaining images in the generated set of images may be spaced evenly between the images corresponding to the boundary slices. Thus, the processor 202 is configured to generate, from the three-dimensional ultrasound scan data, a plurality of images 214, each of the plurality of images corresponding to a respective one of a plurality of slices spaced evenly between the first and second boundaries.

The number of images generated by the processor 202 may be selected by a user or operator or, in the absence of such a selection, a default number of images may be generated. Thus, in some examples, the processor 202 may be configured to receive, via the user interface, an indication of a number of images to be generated as the plurality of images 214. In such examples, the number of images generated as the plurality of images is equal to the indicated number of images. For example, a user may provide an indication via the user interface that 12 images are to be generated, such a selection resulting in the generation of 12 images corresponding to 12 slices of data within the volume defined by the first and second boundaries. In examples where no indication of the number of images to be generated is received by the processor 202, the processor may be configured to generate a default number of images as the plurality of images which, in some examples, may be 8 images. In an example, if first and second boundaries are defined such that the volume within the boundaries has a length of 16 cm, and the processor 202 is to generate a set of 8 images, then the generated images correspond to slices of scan data spaced approximately 2.29 cm apart from one another, including an image corresponding to the slice of data at the first boundary and the slice of data at the second boundary.

The processor 202 is further configured to provide 216 the plurality of images 214 for display to the user. For example, the images may be displayed on a display screen the forms part of the apparatus 200 or a display device that is remote from the apparatus and which can receive data from the processor 202.

Figure 3:
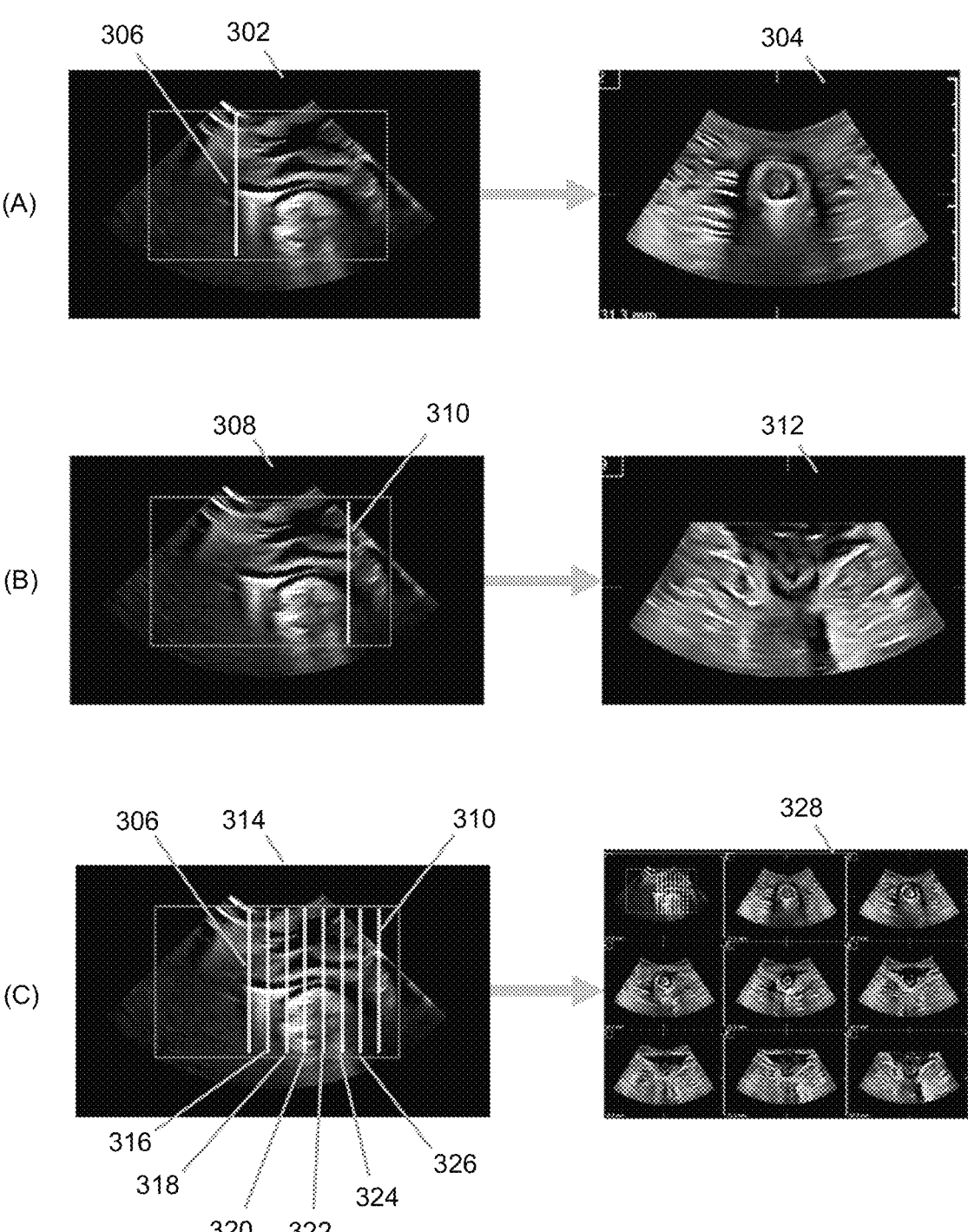
FIG. 3 is an example of various steps involved when processing ultrasound scan data.

FIG. 3 illustrates an example of how a user might provide an indication of the first and second boundaries in three-dimensional ultrasound scan data relating to a volume of a body part of a subject. The part of the body of the subject shown in the images in FIG. 3 corresponds to the subject's anal sphincter. FIG. 3A corresponds to a first step in which the user defines the first boundary of the three-dimensional ultrasound scan data. Image 302 shows a sagittal view of the region of interest which, in this case comprises an anal sphincter. In this example, a user (e.g., a medical professional) may wish to indicate the location of the first and second boundaries so that they correspond to the ends of the anal sphincter (e.g., the IAS and the EAS). The ends of the anal sphincter may be determined using the sagittal view. However, a greater degree of accuracy by additionally referring to a transverse view of the region of interest. Thus, a user may in indicate (e.g., by scrolling or selecting a point in the image using an input device) in the sagittal view (image 302) the apparent location of a first end of the anal sphincter. The user may be presented with an image 304 showing a transverse view of the region of interest (e.g., the anal sphincter) that corresponds to the location indicated in the sagittal view. In the example shown in FIG. 3, the user has provided an indication 306 of the first boundary, shown in this example as a vertical line. The transverse view shown in image 304 corresponds to the location indicated by the line 306.

In some examples, the transverse view shown in the image 304 may change (e.g., in real time) as the user selects a different point in the image 302 or as the user moves a cursor across the image, for example. In this way, the user is able to observe the transverse view of the region of interest alongside the sagittal view, such that a more accurate determination of the end of the anal sphincter can be made. Thus, the processor 202 may be configured to receive, via a user interface (e.g., the user interface 38), a user input indicating a location in the sagittal view of the region of interest. The processor 202 may be further configured to provide for display to the user a transverse view of the region of interest corresponding to the indicated location.

It will be apparent that, while the images shown in FIG. 3 are sagittal views and transverse views, in other examples, other two-dimensional views may be used and displayed.

The user input may be provided in a number of ways. In one embodiment, a line in a predefined direction (e.g., vertical) may be displayed on the first two-dimensional view. The line may be moveable in response to a user input (e.g., scrolling or dragging), and responsive to a further user input (e.g., a click), the line may be fixed to indicate the first or second boundary. In a second embodiment, a user input for indicating the first or second boundary may comprise an indication of a position in the two-dimensional view. Responsive to receiving a user input (e.g., a click or selection), a line may be displayed extending in a predefined direction and passing through the indicated position. This line may represent the first or second border.

FIG. 3B corresponds to a second step in which the user defines the second boundary of the three-dimensional ultrasound scan data. Image 308 shows the sagittal view of the region of interest and, here, the user has provided an indication 310 of the second boundary, shown as a vertical line. The transverse view shown in image 312 corresponds to the location indicated by the line 310.

The first and second boundaries of the ultrasound scan data, which may be referred to as upper and lower boundaries, respectively, may be defined according to the intended use of the ultrasound scan data. The selection of the boundaries may, in some examples, be made based on the position and/or orientation of the subject when the ultrasound scan data was acquired. For example, a three-dimensional ultrasound scan of the anal sphincter may be acquired while the subject is laying in the lithotomy position. In one example, the indication of the first boundary of the three-dimensional ultrasound scan data may comprise an indication of a view of the anal sphincter that corresponds to the most cranial slice of the anal sphincter that does not include the external anal sphincter (EAS) ventrally (i.e., on the side closest to the upper abdomen of the subject). The most cranial slice corresponds to the slice closest to the head of the subject. In some examples, the indication of the second boundary of the three-dimensional ultrasound scan data may comprise an indication of a view of the anal sphincter that corresponds to the most dorsal slice of the anal sphincter that does not include the internal anal sphincter (IAS). The most dorsal slice corresponds to the slice closest to the feet of the subject.

Returning to FIG. 3, the first boundary 306 and the second boundary 310 have been indicated by the user, the spacing between the first and second boundaries can be determined based on the number of images to be generated as the plurality of images. Image 314 shows the first boundary 306 and the second boundary 310, and lines 316 to 326 represent the locations of evenly spaced slices between the first and second boundaries, at which images will be generated to form the plurality of images. Image 328 shows a collage of 9 images, including the image 314 (which includes the sagittal view of the region of interest and lines showing the positions of the plurality of images that are generated) and each of the generated images in the plurality of images. In this example, the image 328 includes 9 images, but it will be apparent that the appearance of the image 328 will vary depending on the number of images in the plurality of images. In some embodiments, the processor 202 may be configured to provide for display to the user, along with the plurality of generated images, the sagittal view of the region of interest including an indication of the location in the sagittal view corresponding to each of the generated images. In other words, an image similar to the image 328 (e.g., with multiple views of the region of interest) may be provided for display to the user.

One or more components of the apparatus 200 disclosed herein may form part of an ultrasound scanning system, such as the ultrasound system shown in FIG. 1. Thus, according to a further aspect, the present invention provides an ultrasound scanning system comprising an apparatus 202 as disclosed herein.

Figure 4:
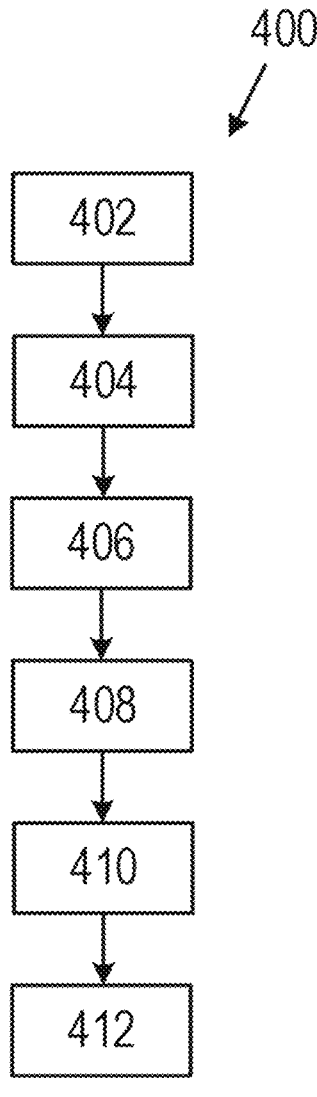
FIG. 4 is a flowchart of an example of a method for processing ultrasound scan data.

According to a further aspect, the present invention provides a method, such as a computer implemented method. FIG. 4 is a flowchart of an example of a method 400, which may comprise a computer-implemented method for processing ultrasound scan data. The method 400 comprises, at step 402, obtaining three-dimensional ultrasound scan data 204 for a volume including a region of interest in a subject. As discussed above, the ultrasound scan data 204 may be obtained from a database 206 or from an ultrasound system or ultrasound scan device 208. At step 404, the method 400 comprises providing the three-dimensional ultrasound scan data for display to a user. Various views of the ultrasound scan data may be provided for display including, for example, one or more two-dimensional views (e.g., sagittal views and/or transverse views).

The method 400 comprises, at step 406, receiving, via a user interface (e.g., the user interface 38), an indication of a first boundary of the three-dimensional ultrasound scan data. The method 400 also comprises, at block 408, receiving, via the user interface, an indication of a second boundary of the three-dimensional ultrasound scan data. At step 410, the method 400 comprises generating, from the three-dimensional ultrasound scan data, a plurality of images 214, each of the plurality of images corresponding to a respective one of a plurality of slices spaced between the first and second boundaries. Step 412 of the method 400 involves providing the plurality of images 214 for display to the user. The plurality of images 214 may then be analyzed by a user, for example to assess the region of interest.

Figure 5:
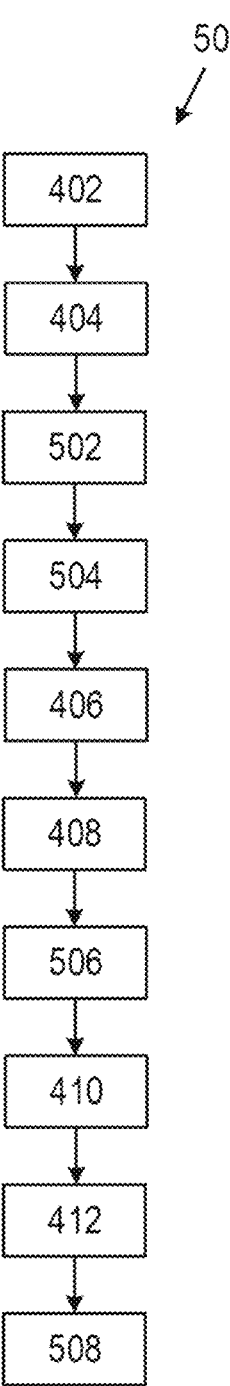
FIG. 5 is a flowchart of a further example of a method for processing ultrasound scan data.

FIG. 5 is a flowchart of a further example of a method 500 (e.g., a computer implemented method), the processing ultrasound scan data. The method 500 may comprise one or more steps of the method 400 discussed above. The step of providing the three-dimensional ultrasound scan data for display to a user (i.e., step 404) may comprise providing for display to the user a first two-dimensional view (e.g., a sagittal view) of the region of interest in a first direction. In some embodiments, the method 500 may further comprise, at step 502, receiving, via a user interface, a user input indicating a location in the first two-dimensional view of the region of interest. At step 504, the method 500 may comprise providing for display to the user a second two-dimensional view (e.g., a transverse view) of the region of interest corresponding to the indicated location. The second two-dimensional view may be in a direction that is perpendicular to the first direction. As discussed above, the second two-dimensional view provided for display to the user may change as the user selects, highlights or otherwise identifies a different location in the first two-dimensional view, thereby enabling them to navigate through the ultrasound scan data, to accurately identify the ends of the region of interest where the first and second boundaries should be indicated. In an example, the transverse view may change as the user manipulates the sagittal view.

In some embodiments, the method 500 may further comprise, at step 506, receiving, via the user interface, an indication of a number of images to be generated as the plurality of images. In the absence of an indication of a number of images to be generated, a default number (e.g., 8 evenly spaced images) may be used. The number of images generated as the plurality of images may be equal to the indicated number of images, or the default number. According to one example, the region of interest may comprise the anal sphincter of the subject. The number of images generated in the plurality of images is 8, either as a result of this number being provided at step 506, or as a result of a default number being used in the absence of an indication. In some examples, the generated images may be provided for display to the user in a grid arrangement. For example, the images may be presented in the manner shown in image 328 of FIG. 3.

At step 508, the method 500 may further comprise providing for display to the user, along with the plurality of generated images, the first two-dimensional (e.g., sagittal) view of the region of interest including an indication of the location in the first two-dimensional (e.g., sagittal) view corresponding to each of the generated images.

Figure 6:
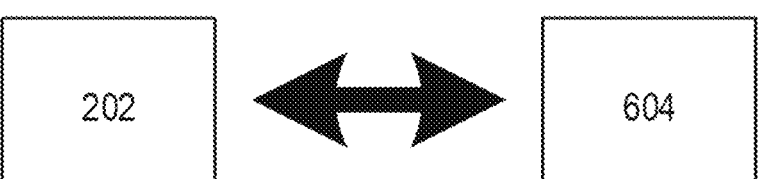
FIG. 6 is a schematic illustration of an example of a processor in communication with a computer-readable medium.

According to a further aspect, the present invention provides a computer program product. FIG. 6 is a schematic illustration of an example of a computer-readable medium 604 and a processor 202. According to some embodiments, a computer program product comprises a non-transitory computer-readable medium 604, the computer-readable medium having computer-readable code embodied therein, the computer-readable code being configured such that, on execution by a suitable computer or processor 202, the computer or processor is caused to perform steps of the methods 400, 500 disclosed herein.

The present disclosure provides an automated mechanism for generating a set of images corresponding to evenly spaced slices of ultrasound data in a set of three-dimensional ultrasound scan data. A process that might previously have been slow and iterative can be greatly improved using embodiments disclosed herein since, with relatively little input from a user, a set of images can be provided that show appropriate parts of a region of interest, for further analysis.

The processor 202 can comprise one or more processors, processing units, multi-core processors or modules that are configured or programmed to control the apparatus 200 in the manner described herein. In particular implementations, the processor 202 can comprise a plurality of software and/or hardware modules that are each configured to perform, or are for performing, individual or multiple steps of the method described herein.

The term "module", as used herein is intended to include a hardware component, such as a processor or a component of a processor configured to perform a particular function, or a software component, such as a set of instruction data that has a particular function when executed by a processor.

It will be appreciated that the embodiments of the invention also apply to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to embodiments of the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g., Java interpreter instructions). Alternatively, one or more or all of the sub-routines may be stored in at least one external library file and linked with a main program either statically or dynamically, e.g., at runtime. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. Measures recited in mutually different dependent claims may be advantageously combined. A computer program may be stored or distributed on a suitable medium, such as an optical storage medium or a solid-state medium supplied together with or as part of other hardware, but may also be distributed in other forms, such as via the internet or other wired or wireless telecommunication systems. Any reference signs in the claims should not be construed as limiting the scope.

The invention claimed is:

1. An apparatus for processing ultrasound scan data, the apparatus comprising: a processor configured to:

obtain three-dimensional ultrasound scan data for a volume including a region of interest in a subject;

provide the three-dimensional ultrasound scan data for display to a user;

receive, via a user interface, an indication of a first boundary of the three-dimensional ultrasound scan data;

receive an indication of a second boundary of the three-dimensional ultrasound scan data;

wherein the processor is further configured to:

provide the three-dimensional ultrasound scan data for display to the user by providing for display to the user a first two-dimensional view of the region of interest in a predetermined direction such that the first two-dimensional view intersects the first boundary;

upon receiving, via the user interface, a user input indicating a location of the first boundary in the first two-dimensional view of the region of interest, generate a second two-dimensional view of the region of
interest corresponding to the first boundary on basis
of the indicated location, and provide for display to
the user the second two-dimensional view of the
region of interest, wherein the first two-dimensional
view and the second two-dimensional view are per-
pendicular to each other; and generate, from the three-dimensional ultrasound scan
data, a plurality of images, each of the plurality of
images corresponding to a respective one of a plu-
rality of slices spaced between the first and second
boundaries, wherein the plurality of images is gen-
erated upon receiving a further user input for trig-
gering the generation of the plurality of images, the
plurality of images also being generated, automati-
cally without receiving the further user input, after a
pre-determined time period in which no user input
for indicating the first boundary, the second bound-
ary, or a combination thereof has been received; and provide the plurality of images for display to the user.

2. An apparatus according to claim 1, wherein the first
two-dimensional view intersects each of the plurality of
slices.

3. An apparatus according to claim 2, wherein the pro-
cessor is configured to:

provide for display to the user, along with the plurality of
images, the first two-dimensional view of the region of
interest including an indication of a location in the first
two-dimensional view corresponding to each of the
plurality of slices.

4. An apparatus according to claim 2, wherein the first
two-dimensional view is perpendicular to each of the plu-
rality of slices.

5. An apparatus according to claim 1, wherein the plu-
rality of slices are parallel to each other.

6. An apparatus according to claim 1, wherein the region
of interest comprises an anal sphincter of the subject.

7. An apparatus according to claim 6, wherein the indi-
cation of the first boundary of the three-dimensional ultra-
sound scan data comprises an indication of a view of the anal
sphincter that corresponds to a most cranial slice of the anal
sphincter that does not include an external anal sphincter
ventrally; and wherein the indication of the second boundary of the
three-dimensional ultrasound scan data comprises an
indication of a view of the anal sphincter that corre-
sponds to a most dorsal slice of the anal sphincter that
does not include an internal anal sphincter.

8. An apparatus according to claim 1, wherein the pro-
cessor is configured to:

receive, via the user interface, an indication of a number
of images to be generated as the plurality of images;

wherein the number of images generated as the plurality
of images is equal to the indicated number of images.

9. An apparatus according to claim 1, further comprising:
the user interface via which one or more user inputs may
be made.

10. An ultrasound scanning system comprising an appa-
ratus according to claim 1 and an ultrasound probe for
acquiring the three-dimensional ultrasound scan data and
providing the acquired three-dimensional ultrasound scan
data to the apparatus.

11. A computer-implemented method for processing ultra-
sound scan data, the method comprising:

obtaining three-dimensional ultrasound scan data for a
volume including a region of interest in a subject;

providing the three-dimensional ultrasound scan data for
display to a user;

receiving, via a user interface, an indication of a first
boundary of the three-dimensional ultrasound scan
data; and receiving an indication of a second boundary of the
three-dimensional ultrasound scan data;

wherein the method further comprises:

displaying a first two-dimensional view of the region of
interest that intersects the first boundary, wherein upon
receiving, via the user interface, a user input indicating
a location of the first boundary in the first two-dimen-
sional view of the region of interest, generating a
second two-dimensional view of the region of interest
corresponding to the first boundary on basis of the
indicated location, and providing for display to the user
the second two-dimensional view of the region of
interest, wherein the first two-dimensional view and the
second two-dimensional view are perpendicular to each
other;

generating, from the three-dimensional ultrasound scan
data, a plurality of images, each of the plurality of
images corresponding to a respective one of a plurality
of slices spaced between the first and second boundar-
ies, wherein the plurality of images is generated upon
receiving a further user input for triggering the genera-
tion of the plurality of images, the plurality of images
also being generated, automatically without receiving
the further user input, after a pre-determined time
period in which no user input for indicating the first
boundary, the second boundary, or a combination
thereof has been received; and providing the plurality of images for display to the user.

12. A computer-implemented method according to claim
11, wherein the region of interest comprises an anal sphinc-
ter of the subject;

the number of images generated in the plurality of images
is 8; and the generated images are provided for display to the user
in a grid arrangement.

13. A computer program product comprising computer-
readable code, the computer-readable code being configured
such that, on execution by a suitable computer or processor,
the computer or processor is caused to perform the method
of claim 11.

* * * * *